United States Patent [19]
Galat

[11] Patent Number: 5,776,431
[45] Date of Patent: Jul. 7, 1998

[54] WATER-SOLUBLE ASPIRIN COMPOSITION

[76] Inventor: Alexander Galat, 126 Buckingham Rd., Yonkers, N.Y. 10701

[21] Appl. No.: 824,429

[22] Filed: Mar. 26, 1997

[51] Int. Cl.$^6$ .................................................. A61K 27/00
[52] U.S. Cl. ........................................................ 424/44
[58] Field of Search ............................................. 424/44

[56] References Cited

U.S. PATENT DOCUMENTS 3,495,001  2/1970  Leonards ................................. 424/44

*Primary Examiner*—Keith D. MacMillan
*Attorney, Agent, or Firm*—Bryan, Levitin & Bab, LLP

[57] ABSTRACT

Compositions in which aspirin is present in combination with alkaline compounds, especially those containing water of crystallization (hydrates), deteriorate on standing. This deterioration may take several forms: It can be a physical deterioration in which such aspirin compositions become completely unmanageable, wet, gummy, sticky masses; or chemical decomposition in which aspirin loses its molecular structure chiefly by losing the acetyl group. The latter is accompanied by formation of acetic acid, the mixture developing its characteristic acetic odor. In both cases, such compositions become entirely unsuitable for all practical commercial and medicinal purposes. Yet, when preparation of water-soluble aspirin compositions is desired, it is impossible to avoid the use of alkaline compounds. This is because the only known method of converting aspirin into soluble form is by means of reacting it with an alkaline compound to form the soluble salt of aspirin. Unexpectedly, it was discovered and is the substance of the present invention that there are two compounds both of which are alkaline and contain water of crystallization (hydrates), and which, in combination with aspirin, give soluble compositions of outstanding stability. These two compounds are sodium citrate (tri) dihydrate, and potassium citrate (tri) monohydrate.

20 Claims, No Drawings

WATER-SOLUBLE ASPIRIN COMPOSITION

FIELD AND BACKGROUND OF THE INVENTION

The present invention relates in general to aspirin compositions, and in particular to a new and useful water-soluble aspirin composition and the method of making the same.

Aspirin is the most widely used drug in the world. It has a number of important uses in medicine: It is a valuable analgesic, antipyretic, and heart-attack and stroke-preventive. It is one of the most potent anti-inflammatory agents, and is the drug of choice and mainstay of arthritis therapy. It stimulates the immune system, reduces opportunistic infections and is potentially useful as an adjunct in treating cancer, AIDS, and other immune disorders. It shows promise in treatment of Alzheimer's Disease; it is used in rheumatic fever, gout and cataracts; it provides pain relief from tendonitis, headaches, backaches, muscle strains, and other injuries. It has a specific analgesic effect in migraine headaches, a condition in which acetaminophen and ibuprofen show no activity. No other drug in the history of medicine has exhibited such an array of multifaceted therapeutic properties.

Despite all these important medical applications, aspirin is known chiefly for its analgesic properties. Its range of application is greatly reduced by virtue of the fact that aspirin is insoluble (sol: 0.3%). Undissolved aspirin particles adhere to the gastrointestinal mucosa, causing well-known side-effects: gastric irritation, inflammation, heartburn, nausea and pain. Such side-effects occur in about 2-10% of aspirin users. In chronic arthritis, they occur in about 25%. Prolonged contact with aspirin particles produces lesions in the mucosa of the mouth, stomach, rectum and in most other mucosal tissues.

An additional disadvantage of aspirin's low solubility is that millions of drug consumers have swallowing problems and need liquid medication. By some estimates, 20% of all adults are affected, including those suffering from arthritis, Parkinsonism, multiple sclerosis, Lou Gehrig's disease and others. It is significant that 30% of the popular acetaminophen product, Tylenol (a trademark), had been in capsule form to facilitate swallowing. (Capsules were discontinued for reasons of criminal tampering and contamination in a publicized poisoning incident.)

Because of these disadvantages, aspirin is not widely used as an anti-inflammatory agent, even though it is actually the mainstay and drug of choice in arthritis—a disease directly caused by inflammation. Instead, its use in arthritis is limited mostly to alleviating pain, for which low 325-500 mg dosages suffice. To be an effective anti-inflammatory agent, daily aspirin dosages of 5,000+ mg are required. At such levels, large amounts of undissolved aspirin particles adhere to the gastrointestinal mucosa, greatly aggravating topical irritation and side-effects.

It is thus clear that a water-soluble form of aspirin, free of the undissolved particles which cause the side-effects mentioned, would be highly desirable. Indeed, efforts to produce it date from the discovery of aspirin itself about a hundred years ago.

A number of soluble aspirin salts were developed and used commercially in the past: lithium ("Hydropyrin"), sodium ("Catalgine"), calcium ("Kalmopyrin," "Ascal," "Dispril," "Kalsetal," "Solaspin," "Solprin," "Tylcasin," "Alcacyl," "Calurin," "Ironin," "Solupsan") and magnesium ("Novacyl", the names in the parentheses being trademarks for products each with the particular salt. None of these products proved satisfactory. Some are toxic (lithium salt). Others are contra-indicated in certain conditions such as hypertension (sodium salt), and still others present undesirable pharmacological side-effects (calcium salts are constipating, magnesium salts are laxative). However, the most important disadvantages of these salts were their difficult and expensive manufacture, unpleasant taste, and lack of stability. Of these disadvantages, the most serious was lack of stability. Consequently, none of these products has survived.

Similarly, the disadvantages of commercial products containing aspirin in soluble form available today are these: "Aspro-Clear" and "Upsarin" are high in sodium; while "Aspegic" contains the unnatural d-form of the amino acid lysine, and could not win regulatory approval in the U.S. Other such products, "Disprin" and "Boots" dissolve incompletely and thus do not solve the problem of gastric irritation caused by undissolved aspirin particles. The names in quotes are also trademarks.

In the U.S., the only commercial product containing aspirin in soluble form is "Alka-Seltzer" (another trademark). However, its use as an anti-inflammatory agent, where daily dosages of 5,000 mg and more are required, would mean ingesting some 9,000-10,000 mg of sodium, making the product unacceptable and even dangerous for many consumers.

The simplest and technically the most feasible, economical way to produce aspirin in soluble form would be to formulate aspirin as a simple mixture with alkaline compounds such as bicarbonates, carbonates, acetates and the like. Unfortunately, such formulations rapidly deteriorate, have a short shelf-life, and are thus unsuitable for commercial use.

This deterioration of aspirin is due chiefly to two factors: Presence of water either in a free state such as moisture, or water combined as water of hydration or crystallization; or the presence of alkaline substances.

These facts are disclosed throughout the technical and patent literature on aspirin. For example, the *Dispensatory of the United States*, 25th ed., p. 16 states:

". . . Hydrolysis occurs in mixtures of aspirin with hygroscopic substances or salts containing water of hydration."

Also, *The Merck Index*, 11th ed., p. 134:

". . . Powders containing aspirin with an alkali salt such as sodium bicarbonate become gummy in the air. Hydrolysis occurs in admixture with salts containing water of crystallization."

These well-known facts of aspirin's incompatibility and vulnerability to decomposition by hydrated and alkaline compounds are confirmed and illustrated by the following examples. In all examples, aspirin mesh #80 was used.

EXAMPLES

The compositions described were all kept at 50°-55° C. This is a generally accepted accelerated aging test. It correctly indicates the probable behavior of such compositions at room temperature. Directly measuring stability at room temperature, while more significant, is impractical, requiring tests of several years' duration.

Example 1

A mixture of 5 g aspirin and 5 g citric acid monohydrate was kept at 50°-55° C. After 40 minutes at this temperature, the mixture became a wet sticky mass and had the odor of acetic acid (the usual decomposition byproduct of aspirin).

Example 2

A mixture of 5 g aspirin and 5 g citric acid anhydrous was kept at 50°–55° for 30 days. In contrast to Example 1 where citric acid monohydrate was used, this mixture, even after 30 days, was unchanged in appearance, and was dry, free-flowing and odorless.

The same deterioration as described in Example 1 was observed with compositions of aspirin with the following hydrates: magnesium chloride hexahydrate, magnesium acetate tetrahydrate, calcium chloride hexahydrate, calcium acetate dihydrate, and sodium phosphate (di) dodecahydrate.

Example 3, below, illustrates the behavior of aspirin in combination with compounds which are both alkaline in nature and contain water of crystallization.

Example 3

The deterioration in Examples 1 and 2 also occurred in aspirin mixtures containing sodium carbonate monohydrate, potassium carbonate sesquihydrate, sodium acetate trihydrate.

Compositions containing aspirin in combination with anhydrous alkaline compounds are equally unstable. Thus, compositions of aspirin with sodium carbonate, potassium carbonate, sodium bicarbonate and potassium bicarbonate all decompose within several hours at 50°–55° C.

The foregoing data show the high instability of compositions containing aspirin in combination with compounds containing water of crystallization (hydrates), or with compounds of alkaline nature, or with compounds that are both of alkaline nature and contain water of crystallization (hydrates).

SUMMARY OF THE INVENTION

The substance of this invention is the discovery of two compounds, which are both alkaline in nature and contain water of hydration and which, in contrast to all other such compounds, may be combined with aspirin to form compositions that are stable for all medicinal, practical and commercial purposes. It was unexpected and surprising to discover that sodium citrate (tri) dihydrate and potassium citrate (tri) monohydrate are two compounds which in combination with aspirin exhibit both solubility in water and outstanding stability.

Accordingly, an object of the present invention is to provide an aspirin composition which is highly soluble in water yet has outstanding stability and shelf life.

A further object of the present invention is to provide a method for making such a composition.

The various features of novelty which characterize the invention are pointed out with particularity in the claims annexed to and forming a part of this disclosure. For a better understanding of the invention, its operating advantages, and specific objects obtained by its uses, reference is made to the following description of preferred embodiments of the invention.

DESCRIPTION OF THE PREFERRED EMBODIMENTS

The following are several examples of various compositions and methods of the present invention:

Example 4

Twenty grams of aspirin were thoroughly mixed with 80 g potassium citrate (tri) monohydrate. The mixture is odorless and free-flowing. It was kept for 30 days at 50°–55° and remained free-flowing and odorless: no decomposition was detected.

Example 5

In this example, 80 g of sodium citrate (tri) dihydrate was used and the same degree of stability was observed.

The high degree of stability of the compositions of Examples 4 and 5 makes them suitable for commercial medicinal applications.

These compositions are readily soluble in water and resulting solutions are complete, clear and palatable. It is emphasized that the completeness of these solutions is crucial since, as mentioned before, it is undissolved aspirin particles which adhere to gastrointestinal mucosa causing aspirin's well-known side-effects (heartburn, irritation, nausea and pain).

When preparing solutions of the compositions of this invention, it is advantageous to add a small amount of surface-active agent.

For example, 0.1 to 0.5% weight of surface-active agent can be used with 10% weight aspirin, 20% to 40% weight hydrated salt, all in about 150 ml water.

Example 6

Twenty grams of aspirin, 80 g potassium citrate (tri) monohydrate, and 20 mg of sodium lauryl sulfate (commercially available under the trademark "Empicol") are thoroughly mixed together. In order to administer a 500-mg dose of aspirin, 2.5 g of this composition are dissolved in 150 ml water. The solution is complete, clear and palatable.

Example 7

Twenty grams of aspirin, 80 g sodium citrate (tri) dihydrate, and 20 mg of "Empicol" are thoroughly mixed together. In order to administer a 500-mg dose of aspirin, 2.5 g of this composition are dissolved in 150 ml water. The solution is complete, clear and palatable.

While compositions containing sodium citrate (tri) dihydrate and potassium citrate (tri) monohydrate are both hydrated salts (tri) of citric acid, and suitable for aspirin therapy, the composition of Example 6 has the advantage of being sodium-free. Since arthritis is a disease afflicting the elderly in particular, and because they are often on sodium-restricted diets, this composition may be preferred.

While specific embodiments of the invention have been shown and described in detail to illustrate the application of the principles of the invention, it will be understood that the invention may be embodied otherwise, without departing from such principles.

What is claimed is:

1. A water-soluble and stable composition comprising: aspirin; and hydrated salts (tri) of citric acid with metals of the alkaline group.

2. The composition of claim 1 wherein the alkaline group consists of sodium and potassium.

3. The composition of claim 2 wherein the hydrated salts (tri) of citric acid are selected from the group consisting of potassium citrate (tri) monohydrate and sodium citrate (tri) dihydrate.

4. The composition according to claim 3 containing about 10% by weight aspirin and from about 20% to about 40% by weight hydrated salt, in about 150 ml water.

5. The composition of claim 3 comprising a water solution containing about 10% by weight aspirin, from about 20% to about 40% by weight hydrated salt, in about 150 ml water.

6. The composition of claim 5 including from 0.1% to 0.5% by weight surface-active agent.

7. The composition of claim 6 wherein the surface-active agent is sodium lauryl sulfate.

8. The composition of claim 1 wherein the hydrated salt comprises sodium citrate (tri) dihydrate.

9. The composition of claim 1 wherein the hydrated salt comprises potassium citrate (tri) monohydrate.

10. The composition of claim 1 comprising a solution of acid with dehydrated salt and water.

11. The composition of claim 10 including a surface-active agent in the solution.

12. The composition of claim 1 consisting essentially of about 10% by weight aspirin and from about 20% to 40% by weight hydrated salts, all in water, the hydrated salts selected from the group consisting of sodium citrate (tri) dihydrate and potassium citrate (tri) monohydrate.

13. The composition of claim 1 including about 150 ml water.

14. A method of making a water-soluble and stable composition containing aspirin, comprising:

Combining aspirin with a hydrated salt (tri) of citric acid with metals of the alkaline group.

15. A method according to claim 14 wherein the hydrated salts are selected from the group consisting of sodium citrate (tri) dihydrate and potassium citrate (tri) monohydrate.

16. A method according to claim 15 comprising dissolving the mixture of aspirin and hydrated salts in water.

17. The method according to claim 16 including combining in the solution a surface-active agent.

18. A method according to claim 14 comprising dissolving the aspirin with hydrated salts in water.

19. A method according to claim 18 including utilizing from about 10% by weight aspirin with about 20% to about 40% by weight hydrated salts in water.

20. A method according to claim 19 including dissolving the combination of aspirin and hydrated salts in water and adding from 0.1% to 0.5% by weight surface-active agent.

* * * * *